United States Patent [19]

Monget et al.

[11] 4,277,561

[45] Jul. 7, 1981

[54] SUPPORT FOR THE DETERMINATION OF ENZYME ACTIVITIES AND PROCESS

[75] Inventors: Daniel Monget; Paul Nardon, both of Villeurbanne, France

[73] Assignee: Laboratoire de Recherche API, La Balme-les-Grottes, France

[21] Appl. No.: 769,277

[22] Filed: Feb. 16, 1977

[30] Foreign Application Priority Data

Feb. 19, 1976 [FR] France .................................. 76 05165

[51] Int. Cl.³ .......................... C12Q 1/54; C12Q 1/42; C12Q 1/00; C12M 1/20
[52] U.S. Cl. .......................................... 435/14; 435/4; 435/18; 435/19; 435/21; 435/23; 435/24; 435/29; 435/301; 435/805; 435/287; 23/230 B; 422/56; 422/99
[58] Field of Search ...................... 195/99, 103.5, 127; 23/230 B, 253 TP; 424/2, 7, 8, 9, 12, ; 435/4, 14, 18, 19, 21, 23, 24, 29, 805, 301, 287; 422/56, 57, 58, 99

[56] References Cited

U.S. PATENT DOCUMENTS

| 3,043,669 | 7/1962 | Charles .......................... 195/103.5 R |
| 3,552,925 | 1/1971 | Fetter .................................. 23/230 B |
| 3,616,251 | 10/1971 | Linoli ............................ 195/103.5 R |
| 3,764,479 | 10/1973 | Bergeron et al. ............. 195/103.5 R |
| 3,842,166 | 10/1974 | Bucalo .............................. 195/127 X |
| 3,843,324 | 10/1974 | Edelman et al. ................... 23/230 B |
| 3,963,442 | 6/1976 | Bullard et al. .................... 23/253 TP |
| 4,038,149 | 7/1977 | Liner et al. ........................... 195/127 |

Primary Examiner—Thomas G. Wiseman
Attorney, Agent, or Firm—Karl F. Ross

[57] ABSTRACT

A support and method for the determination of enzyme activity in a biological extract is provided wherein the support comprises a fibrous material impregnated with a substrate and a water-soluble pH stabilizer comprising a first reagent suitable for a pH of enzyme activity over 7 or a second reagent suitable for a pH of enzyme activity of 7 or less; the viscose fibers are sufficiently loose in texture so as to be accessible both to products in solution and to tissuey and cellular mash or whole cells and sufficiently fine to permit adsorption and uniform distribution of reagents over the area thereof.

The method comprises:
 (a) preparing a biological extract of the enzyme to be determined;
 (b) depositing a sample thereof on the support;
 (c) incubating said sample; and
 (d) placing on the support a developing reagent comprising a wetting agent and a buffer, and a coloring agent whereby the reactions are brought to a fixed pH, said pH being optimal for the colorimetric reaction between the substrate and the coloring agent.

16 Claims, 4 Drawing Figures

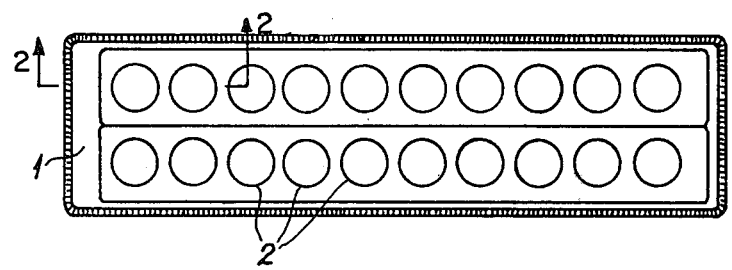
FIG_1
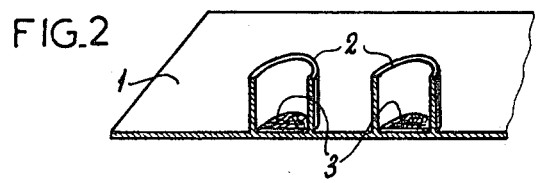
FIG.2
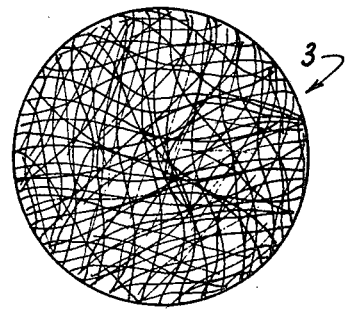
FIG_3
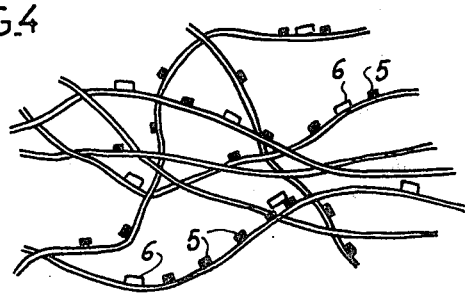
FIG.4

SUPPORT FOR THE DETERMINATION OF ENZYME ACTIVITIES AND PROCESS

BACKGROUND OF THE INVENTION

The present invention relates to a support for the determination of enzyme activities and to a method for such determination employing said support.

It is known that paper discs may be used to perform chemical tests, such as strip tests for albumin, glucose and or disc tests for antibiotics, ONPG and the like wherein the reagent is simply placed on a sheet of paper. These are approximate methods, and do not serve to provide quantitative results.

Traditional methods of precision analysis call for complicated and costly apparatus and are time-consuming.

For the conventional determination of enzyme activity, it has been necessary to prepare a purified biological extract and an aqueous buffer with a pH corresponding to the pH of the activity of the enzyme, for each activity. This means that as many buffers must be prepared as there are optimum pH-values of activity, when several enzymes acting at different pH-values are to be determined.

Moreover, if the substrate is to be dissolved in the buffer, the use of substrates insoluble in water is excluded. If the substrate is not directly chromogenic, a coloring agent must be prepared and the so-formed colored product of the determination must itself be soluble in aqueous media. This excludes all substrates that yield water-insoluble reaction products. In addition, for each activity tested, the substrate, the biological extract in the buffer and other reagents such as the coloring agent must be mixed in proper proportions. Finally, since these reactions are determined spectrophotometrically, a photometer must be employed.

Besides the need for comparatively costly apparatus, such a procedure is very time-consuming in practice, since as a rule no result can be obtained until after several days of experiments carried out by a qualified technician. It also has the disadvantage of requiring a comparatively large quantity of the biological extracts to be tested.

The present invention on the other hand provides a novel apparatus and method to perform the determination of enzyme activities quickly and simply. It is not the purpose of the present invention to attain the precision of spectrophotometric determinations for each enzyme, but it is intended essentially for detection of enzyme activities in an unpurified complex extract. Neither is the invention intended to take the place of electrophoretic separating methods. The present invention rather serves as an excellent guide for the latter by previously giving the spectrum of enzyme activities of the sample to be tested in its crude state.

SUMMARY OF THE INVENTION

According to one aspect of the present invention a support for the determination of enzyme activities is provided comprising a fibrous material impregnated with a substrate and a water-soluble pH stabilizer comprising a first reagent suitable for a pH of enzyme activity over 7 or a second reagent suitable for a pH of enzyme activity of 7 or less.

The fibrous material of the present invention can be for example a sheet of viscose or cellulosic fibers such as rayon which has the following properties:
(a) chemically inert and generally insoluble in organic solvents;
(b) loose in texture, so as to be completely accessible both to products in solution and to tissuey and cellular mash or whole cells;
(c) sufficiently fine to permit adsorption and uniform distribution of reagents over the entire area, when the sheet is impregnated with an alcoholic solution containing at least one reagent or substrate and one pH stabilizer highly soluble in water;
(d) permits adjustment of the pH to that of the reaction in question without interfering with the latter;
(e) does not affect the stability of the reagents with which the fibers are impregnated;
(f) affords a good wetting action regardless of hydrophobic properties of the reagents, all molecules of which are rendered accessible to the reaction.

The substrate or substance acted upon by the enzyme is based on naphthol or derivatives thereof and is impregnated on the support as an alcoholic solution. A number of these substrates are listed in Table I (infra).

The first reagent suitable for pH's of enzyme activities over 7 can be tris-HCl and the second reagent suitable for pH's of 7 or less can be tris-sodium maleate.

In a preferred embodiment of the support of the present invention, the support consists of a plurality of discs placed in the bottoms of a corresponding number of cups fashioned in a tray made of a material impervious to the experimental conditions.

According to another aspect of the invention a method for determining enzyme activities employing the above support is provided comprising:
(a) preparing a biological extract of the enzyme to be determined;
(b) depositing a sample thereof on the support;
(c) incubating said sample; and
(d) placing on the support a developing reagent comprising a wetting agent and a buffer, and a coloring agent whereby the reactions are brought to a fixed pH, said pH being optimal for the colorimetric reaction between the substrate and the coloring agent.

Preferred among useful coloring agents are azo dyes. The present apparatus and method serve to bring out simultaneously, in the case of a support with n cups, n−1 enzyme reactions (one of the cups being the control) in a minimum of time and with a small quantity of media to be tested.

The present method can be carried out easily and efficiently, consisting as it does merely in preparing the extract in distilled water. All kinds of substrates may be used, including substrates insoluble in water, which is a great advantage over conventional solutions. Among such substrates, use may be made of those with which an insoluble or colored final reaction product is obtained, as is the case of the azo derivatives obtained after coupling of a naphthol with a diazonium salt.

Advantageously, the developing reagent is a surface-active agent tending to favor release of the naphthol retained by the fibers and to solubilize the granular complex formed by the azo dye.

By way of example, the developing reagent may consist of:
250 g tris-(hydroxymethyl)-aminomethane
110 ml hydrochloric acid 37%

100 g lauryl sulfate
distilled water in sufficient quantity for 1000 ml

After allowing the developing reagent to act, it is desirable to insulate the support naturally or artificially so as to destroy, for example, the diazonium salt molecules in excess without modifying the coloring of the azo complex formed. This will permit a photometric determination by reflectometry.

BRIEF DESCRIPTION OF THE DRAWING

The accompany drawing illustrates a support according to the present invention. Therein:

FIG. 1 is a top view of a support consisting of a plurality of discs located in the bottoms of a corresponding number of cups, all arranged within a tray;

FIG. 2 is a section of FIG. 1 at line 2—2;

FIG. 3 is an enlarged view of a disc of FIG. 1; and

FIG. 4 is an enlarged view of a disc portion of FIG. 3 after impregnation with the alcoholic solution containing the reagents.

DETAILED DESCRIPTION OF THE PREFERRED EMBODIMENTS

The support 1 shown in FIGS. 1 and 2 consists of a tray made of a material impervious to and insoluble in ordinary organic solvents, in which are fashioned 20 cups 2. In the bottom of each cup is placed a disc 3 made of a paper sheet of viscose fibers. (See FIGS. 3 and 4.) As shown particularly in FIGS. 3 and 4, these fibers are very fine and loose in texture, so that they are all accessible both to the products in solution and to tissuey and cellular mash as well as whole cells.

FIG. 4 shows the regular distribution of buffer molecules 5 and substrate molecules 6 on some portions of fibers 4.

Generally, in carrying out the method of determining enzyme activity using the support of the invention, an individual incubating box is prepared and about 5 ml of water is placed in the cells of the box. The support tray of FIG. 1 for example is then placed in the box, the box being marked for identification. A sample containing the enzyme to be determined is diluted with a volume of at least 2 ml of distilled water or unbuffered aqueous media such as physiological saline solution.

Depending on the nature of the sample to be determined, there are various methods of preparing it.

(a) For microorganisms, a dense suspension must be prepared, optical density 5–6 (McFarland scale), in a survival medium, from a gelose (amorphous polysaccharide from agar) transfer of a pure culture or a centrifuge cell for a culture in liquid medium. To obtain reproducible results, it is important that the strains to be compared be previously cultured on a similar medium; that the suspensions be made in the same liquid; and that they have the same optical density. Such a procedure will serve to detect constitutive enzymes; induced enzymes can be detected by adding the corresponding inducer or inducers to the culture medium.

(b) For cell suspensions, such as cultures of cells, spermatozoa and the like, the centrifuge cell must be flushed with distilled water to arrive at a known cell concentration ($10^5$ to $10^7$ per ml depending on intensity of enzyme activities of sample).

(c) For tissues, the sample must be mashed in distilled water using a Poter tube. The amount of sample required is on the order of a few milligram. and (d) For biological fluids, it is possible to use the raw fluid or a solution in distilled water if the available samples are small or if the enzyme activity of the raw fluid is too high.

When the sample has been prepared, it is distributed on the support tray with a Pasteur pipette at the rate of two drops (65 microliters) per cup.

The insulator is closed and incubated for a few hours at an optimal temperature (generally 4 hours at 37° C.). The conditions of time and temperature may of course vary according to the sample as is well known in the art.

At the end of the incubation period, a solution containing the developing reagent and a dye such as Fast Blue BB (Sigma F 0250-SIGMA CHEMICAL COMPANY) is prepared, generally about 35 mg Fast Blue to 10 ml reagent. The reagent must be kept at room temperature, and the Fast Blue powder must be kept at $+4°$ C. in darkness, and the mixture must be freshly prepared. With the reaction support tray placed away from direct light, the developing is carried out by adding a drop of the aforesaid solution to each cup.

The colorings are allowed to develop for about 5 minutes, after which the operator exposes the tray to the rays of a very strong light (around 1000 watts and 3400° K.) placed some 10 centimeters from it for about 10 seconds. The purpose of this operation is to eliminate the yellow background due to unreacted excess of Fast Blue and thereby render colorless those cups in which the reactions are negative. Of course, some minutes of exposure to solar radiation will have the same effect.

It will then suffice to take the readings and rate the results obtained for each cup from 0 to 5 for example: a zero rating corresponds to a negative reaction, whereas a rating of 5 corresponds to a rating of maximum intensity. The colorings thus obtained will remain stable for several hours. Although the analysis by direct reading is sufficiently accurate, it can be confirmed by measuring the intensity of the various colorings with a photometer.

Table I below provides a list of substrates, corresponding enzymes, and colorings obtained in the case of positive reactions.

TABLE I

| N° | ENZYME TESTED | SUBSTRATE | pH | REACTION Positive | Negative |
|---|---|---|---|---|---|
| 1 | Control | | | | Colorless, or color of sample if appreciably colored |
| 2 | Phosphatase alkaline | 2 naphthyl phosphate | 8.5 | Violet | Colorless, |
| 3 | Esterase (C 4) | 2 naphthyl butyrate | 7.1 | Violet | or color of |
| 4 | Esterase Lipase (C 8) | 2 naphthyl caprylate | " | Violet | control if |
| 5 | Lipase (C 14) | 2 naphthyl myristate | " | Violet | layout has |
| 6 | Leucine aminopeptidase | L leucyl 2 naphthylamide | 7.5 | Orange | been exposed |
| 7 | Valine aminopeptidase | L valyl 2 naphthylamide | " | Orange | to an intense |
| 8 | Cystine aminopeptidase | L cystyl 2 napthylamide | " | Orange | light source |
| 9 | Trypsine | N benzoyl DL arginine 2 naphthylamide | 8.5 | Orange | after addition of reagents |

TABLE I-continued

| N° | ENZYME TESTED | SUBSTRATE | pH | REACTION Positive | Negative |
|----|---------------|-----------|-----|----------|----------|
| 10 | Chymotrypsine | N benzoyl Dl phenylalnine 2 naphthylamide | 7.1 | Violet | Very pale yellow if this has not been done |
| 11 | Phosphatase acid | 2 naththyl phosphate | 5.4 | Violet | |
| 12 | Phosphoamidase | naphthol AS BI phosphodiamide | " | Blue | |
| 13 | α galactosidase | 6 Br 2 naphthol D galactopyranoside | " | Violet | |
| 14 | β galactosidase | 2 nathyl B galactopyranoside | " | Violet | |
| 15 | β glucuronidase | naphthol AS BI D glucuronnic acid | " | Blue | |
| 16 | α glucosidase | 2 naththyl D glucopyranoside | " | Violet | |
| 17 | β glucosidase N acetyl | 6 Br 2 naphtol D gluco-pyranoside | " | Violet | |
| 18 | β glucosaminidase | 1 naphthyl N acetyl D glucosaminide | " | Maroon | |
| 19 | α mannosidase | 6 Br 2 naphtol D mannopyranoside | " | Violet | |
| 20 | α fucosidase | 2 naphthyl L fucopyranoside | " | Violet | |

The invention will be further illustrated in the following examples

EXAMPLE 1

Bacterial Enzymology—Detection of beta-galactosidase

Because of its solubility in water, ONPG can penetrate bacteria and is able to induce beta-galactosidase. In the case of a positive reaction, there is then no way to discriminate between the induced and the constitutive nature of the enzyme.

On the other hand, the support according to the invention, impregnated with substrates insoluble in water and hence not penetrating the cells, will differentiate the two cases.

Thus with a naphthyl beta-galactoside, only a constitutive beta-galactosidase of the bacteria can be manifested. If the enzyme is present only in induced form, an inducer need only be added to reveal its presence.

Thus it becomes quite simple not only to detect the enzyme, but also, by the method of developing appropriate to the support, to determine the activity by means of a reflectometer, with a precision comparable to that of conventional biochemical methods.

EXAMPLE 2

Enzymology of Biological Fluids—Detection of Alkaline Phosphatase

The use of paranitrophenol substrate discs will not provide a sufficiently accurate visual estimate of enzyme activities, the eye being quite insensitive to the yellow coloration of the paranitrophenol.

On the other hand, the eye can very readily detect any naphthyl concentration equal to or greater than 20 micromols per liter, owing to the very good visualization of azo dyes (for paranitrophenol, this concentration limit is no less than 200 micromols).

The use of naphthol-base enzyme substrates deposited on the support according to the invention substantially increased the sensitivity of the determination of enzyme activity, because of the improvements in the method of developing.

This serves greatly to diminish the volume of biological fluid required for detecting and estimating an activity. This point is the more important because very often only a very small quantity of extract is available for such a determination.

With 1 microliter of uterine secretion, amniotic fluid or human serum, this method will show up alkaline phosphatase activity using a naphthyl phosphate as in substrate. The 1 microliter need only be diluted with 0.1 ml water to be placed on the disc impregnated with substrate and alkaline buffer.

EXAMPLE 3

Cell Enzymology

The use of several discs each impregnated with a different naphthol enzyme substrate and the pH stabilizer suited to the enzyme sought allows for simultaneous detection and determination of as many activities as there are discs, from a single cell suspension in water, regardless of the number of optimum pH values of the activities.

This technique of simultaneous determination from a single extract has been successfully tried on human spermatozoa and also on cancer-cell cultures.

With only 2 ml of aqueous suspension, 20 activities were tested at the same time, such as acid and alkaline phosphatases, phosphoamidase, esterases, lipases, 4 aminopeptidases, trypsin and chymotrypsin, alpha- and beta-galactosidases, beta-glucuronidase, N acetyl, beta-glucosaminidase, alpha-fucosidase, alpha-mannosidase, beta-xylosidase. These twenty enzyme reactions were brought forward merely because the treatment of the support provides all the required conditions for each (pH, substrate concentration etc.).

The multiplicity of tests performed and the speed with which they are carried out thus provided a large number of data on cell metabolism. Such a result cannot be obtained in any other way.

EXAMPLE 4

Comparison of Two Strains of Cancer Cells

These are two cell types very close to each other—morphologically indistinguishable lymphocytes from a Burkitt's lymphoma. Differential diagnosis would be possible only by very complicated immunological methods. The HR 1K strain is virus-producing (only 5 to 7% of cells) and the NUNN strain is not.

To identify the two strains:

The cells were taken from a four-day culture and centrifuged to separate the cells from the culture medium. Next the cells were flushed and returned to a suspension in distilled water to obtain a density of $9 \times 10^6$ cells/ml for the two strains. Since only 2 ml is enough to carry out the reaction, this was not a very large number of cells. In each of the 20 cups of a tray according to FIG. 1 was distributed 2 drops (65 microliters) of the suspension. This amounts to about 600,000 cells per cup for a test (in ordinary practice, it is not unusual to employ over 2 million cells for a test). The tray was incubated in a moist box at 37° C. for 4 hours. These five operations represented 30 to 45 minutes of work for one person. After 4 hours, a drop of developing reagent was added to each cup and after leaving the tray in darkness for about 5 minutes, the tray was exposed for 10 seconds to a 1000 W 3400° K. photographic bulb (or to the sun). The intensities of each reaction were read off, rating from 0 (negative reaction) to 5 (maximum reaction) according to a previously prepared color scale. The results obtained are shown in Table II below.

TABLE II

| Enzyme | Intensity of the coloration NUNN Strain | Intensity of the coloration HR1K Strain |
|---|---|---|
| Phosphatase alcaline | 3 | *0 |
| Phosphodiamidase | 2 | *0 |
| Esterase I | 4 | *3 |
| Esterase II | 3 | *2 |
| Lipase I | 2 | 1.5 |
| Lipase II | 0 | 0 |
| Lipase III | 0 | 0 |
| Leucine aminopeptidase | 3 | 3 |
| Valine aminopeptidase | 1.5 | 1 |
| Phenylalanine aminopeptidase | 3 | 2.5 |
| Trypsine | 0 | 0 |
| Chymotrypsine | 0 | 0 |
| β galactosidase | 1 | *0 |
| α galactosidase | 0.5 | 0 |
| β glucuronidase | 1 | 0.5 |
| β glucosaminidase | 2 | *1.5 |
| β glucosidase | 1 | *0 |
| α glucosidase | 0.5 | 0 |
| α mannosidase | 0.5 | *0 |
| α fucosidase | 1 | *0.5 |
| β xylosidase | 0 | 0 |
| Phosphatase acid | 5 | *2 |
| TOTAL | 34 | 17.5 |

Thus in about five hours it was possible to complete a differential diagnosis between two strains of lymphocytes. By conventional methods, such a diagnosis would require at least a week of work, and would be incomparably more expensive.

The diagnosis can be confirmed by doing another 18-hour incubation and rating the intensities of reaction with a reflectometer.

We claim:

1. A support for the determination of enzyme activity in a biological extract comprising a fibrous material impregnated with a substrate labeled with a naphthol and a buffer solution selected from the group consisting of a first buffer solution suitable for a pH of enzyme activity over 7 and a second buffer solution suitable for a pH of enzyme activity of 7 or less and free from color developing agents; said fibrous material being loose in texture so as to be accessible both to products in solution and to said biological extract consisting of tissuey and cellular mash or whole cells and sufficiently fine to permit adsorption and uniform distribution of reagents over the area thereof; and said naphthol substrate originally being colorless or pale yellow so that any subsequent coloration of the substrate, which results from coupling of said naphthol released therefrom with a diazonium salt color-developing agent to indicate the presence of enzyme activity, is readily apparent.

2. The support of claim 1 wherein said fibrous material is a sheet of viscose fibers.

3. The support of claim 1 wherein the first buffer solution suitable for a pH of enzyme activity over 7 is tris-HCl.

4. The support of claim 1 wherein the second buffer solution suitable for a pH of enzyme activity of 7 or less is tris-sodium maleate.

5. An apparatus for determining enzyme activity in a biological extract comprising:
(a) a tray having a plurality of cups contained therein; and
(b) a plurality of discs located in the bottom of said cups, said discs being composed of a fibrous material impregnated with a substrate labeled with a naphthol and a buffer solution selected from the group consisting of a first buffer solution suitable for a pH of enzyme activity over 7 and a second buffer solution suitable for a pH of enzyme activity of 7 or less, and free from coloring agents; said fibrous material being loose in texture so as to be accessible both to products in solution and to biological samples of tissuey and cellular mash or whole cells and sufficiently fine to permit adsorption and uniform distribution of reagents over the area thereof and said naphthol substrate originally being colorless or pale yellow so that any subsequent coloration of the substrate, which results from coupling of the naphthol released therefrom with a diazonium salt color-developing agent to indicate the presence of enzyme activity, is readily apparent.

6. The apparatus of claim 5 wherein said fibrous material is a sheet of viscose fibers.

7. The apparatus of claim 5 wherein the first buffer solution suitable for a pH of enzyme activity over 7 is tris-HCl.

8. The apparatus of claim 5 wherein the second buffer solution suitable for a pH of enzyme activity of 7 or less is tris-sodium maleate.

9. A method of determining enzyme activity comprising:
(a) preparing a biological extract of the enzyme whose activity is to be determined;
(b) depositing a sample of said extract on a support comprising a fibrous material impregnated with a substrate labeled with a naphthol and a buffer solution selected from the group consisting of a first buffer solution suitable for a pH of enzyme activity over 7 and a second buffer solution suitable for a pH of enzyme activity of 7 or less, and free from color-developing agents; said fibrous material being loose in texture so as to be accessible both to products in solution and to biological samples of tissuey and cellular mash or whole cells and sufficiently fine to permit adsorption and uniform distribution of reagents over the area thereof; said substrate originally being colorless or pale yellow so that any subsequent coloration of the substrate, which results from coupling of the naphthol released therefrom with a color-developing agent to indicate the presence of enzyme activity, is readily apparent;
(c) incubating said sample;
(d) depositing on said support a developing reagent comprising a wetting agent, a buffer suitable for use at the desired pH and a diazonium salt color-developing agent for coupling with said released naphthol whereby the reactions are brought to a pH optimal for the colorimetric reaction between said substrate and said color-developing agent;

(e) photochemically decomposing any unreacted color-developing agent; and (f) comparing said color reactions to a color scale indicative of the activity of the enzyme.

10. The method of claim 9 wherein said fibrous material is a sheet of viscose fibers.

11. The method of claim 9 wherein the first buffer solution for a pH of enzyme activity over 7 is tris-HCl.

12. The method of claim 9 wherein the second buffer solution suitable for a pH of enzyme activity of 7 or less is tris-sodium maleate.

13. The method of claim 9 wherein the developing reagent contains a surface-active agent tending to favor release of naphthol retained by said fibers and to solubilize a granular complex formed by said diazonium salt.

14. The method of claim 9 wherein the diazonium salt coloring agent is Fast Blue BB, said agent present in the reagent in proportions of 35 mg to 10 ml of reagent.

15. The method of claim 9, further comprising treating said support after addition of said reagent so as to destroy excess diazonium salt molecules without affecting the coloration of the azo dye complex formed, thereby permitting photometric determination of enzyme activity by reflectometry.

16. The method of claim 9 wherein the developing reagent consists of an aqueous solution of:
tris-(hydroxymethyl)-aminomethane;
37% hydrochloric acid; and
lauryl sulfate.

* * * * *